(12) United States Patent
De Groot et al.

(10) Patent No.: US 7,030,995 B2
(45) Date of Patent: Apr. 18, 2006

(54) APPARATUS AND METHOD FOR MECHANICAL PHASE SHIFTING INTERFEROMETRY

(75) Inventors: Peter J. De Groot, Middletown, CT (US); Leslie L. Deck, Middletown, CT (US)

(73) Assignee: Zygo Corporation, Middlefield, CT (US)

( * ) Notice: Subject to any disclaimer, the term of this patent is extended or adjusted under 35 U.S.C. 154(b) by 0 days.

(21) Appl. No.: 10/304,426

(22) Filed: Nov. 26, 2002

(65) Prior Publication Data

US 2003/0137671 A1    Jul. 24, 2003

Related U.S. Application Data

(60) Provisional application No. 60/339,098, filed on Dec. 10, 2001.

(51) Int. Cl.
*G01B 9/02* (2006.01)

(52) U.S. Cl. ...................................... 356/512

(58) Field of Classification Search ............... 356/511, 356/512, 513, 514, 516, 497, 495, 450
See application file for complete search history.

(56) References Cited

U.S. PATENT DOCUMENTS

| | | | | |
|---|---|---|---|---|
| 3,708,229 A | * | 1/1973 | Pircher | 356/516 |
| 4,594,003 A | | 6/1986 | Sommargren | |
| 4,732,483 A | * | 3/1988 | Biegen | 356/495 |
| 5,229,304 A | * | 7/1993 | Chang et al. | 438/7 |
| 5,231,468 A | * | 7/1993 | Deason et al. | 356/513 |
| 5,303,033 A | * | 4/1994 | Matsuzaki | 356/515 |
| 5,398,113 A | | 3/1995 | de Groot | |
| 5,473,434 A | * | 12/1995 | de Groot | 356/514 |
| 5,557,408 A | * | 9/1996 | Kanaya | 356/514 |
| 5,671,050 A | * | 9/1997 | de Groot | 356/497 |
| 5,739,906 A | * | 4/1998 | Evans et al. | 356/503 |
| 6,006,128 A | | 12/1999 | Izatt et al. | |
| 6,028,670 A | * | 2/2000 | Deck | 356/497 |
| 6,359,692 B1 | | 3/2002 | de Groot | |
| 6,597,460 B1 | * | 7/2003 | Groot et al. | 356/512 |

(Continued)

FOREIGN PATENT DOCUMENTS

WO    WO 02/12825    2/2002

OTHER PUBLICATIONS

L. Deck; "Measurements using Fourier-Transform Phase Shifting Interferometry", Proc. ASPE 25, 115-118 (2001).

(Continued)

*Primary Examiner*—Gregory J. Toatley, Jr.
*Assistant Examiner*—Michael A. Lyons
(74) *Attorney, Agent, or Firm*—Fish & Richardson P.C.

(57) ABSTRACT

An interferometry method including: i) forming an optical interference image by combining different portions of an optical wave front reflected from a pair of surfaces; ii) recording an interference signal at different locations of the optical interference image in response to varying the relative position of the two surfaces over a range of positions; iii) transforming the interference signal for at least one of the locations to produce a spectrum having a peak at a spectral coordinate corresponding to the variation in the relative position of the two surfaces over a range of positions; iv) identifying the spectral coordinate of the peak; and v) for each location, extracting the spectral phase of the interference signal at the coordinate of the peak. For example, the method may further include, for each of the different locations, determining a surface profile of one of the surfaces based on the spectral phase of the interference signal at each of the multiple locations.

20 Claims, 1 Drawing Sheet

U.S. PATENT DOCUMENTS 6,643,024 B1 * 11/2003 Deck et al. .................. 356/496

OTHER PUBLICATIONS

L. Deck; "Multiple Surface Phase Shifting Interferometry", Proc. SPIE, 4451, 424-430 (2001).

L. Deck and J.A. Soobitsky, "Phase-shifting via wavelength tuning in very large aperture interferometers," Proc. SPIE, 3782-58, 432-442, 1999.

L. Deck; "Simultaneous Multiple Surface Measurements using Fourier-Transform Phase Shifting Interferometry, in: 4th International workshop on automatic processing of fringe patterns", Fringe 2001, Elsevier, Paris, (2001), 230-236.

P. de Groot, "Chromatic dispersion effects in coherent absolute ranging," Opt. Lett., vol. 17, pp. 898-900, 1992.

Peter de Groot, "Derivation of algorithms for phase-shifting interferometry using the concept of a data-sampling window," Applied Optics, vol. 34, p. 4723, 1995.

Peter de Groot, "Measurement of transparent plates with wavelength-tuned phase-shifting interferometry," Applied Optics, vol. 39, No. 16, pp. 2658-2663, 2000.

Klaus Freischlad, "Fourier Analysis of Phase Shifting Algorithms," Proc. SPIE vol. 3407, pp. 73-85, 1998.

K. Freischlad, "Large flat panel profiler," Proc. SPIE 2862, pp. 163-171, 1996.

J.E.Greivenkamp and J.H.Bruning, "Phase shifting interferometry," Optical Shop Testing, D. Malacara, pp. 501-598, J. Wiley, New York, 1992.

Susumu Kuwamaura and Ichirou Yamaguchi, "Wavelength scanning profilometry for real-time surface shape measurement," Appl. Opt., 36, 4473-4482 (1997).

Okada et al., "Separate measurements of surface shapes and refractive index inhomogeniety of an optical element using tunable-source phase shifting interferometry," Applied Optics, vol. 29, No. 22, pp. 3280-3285, 1990.

M. Suematsu and M. Takeda, "Wavelength-shift interferometry for distance measurements using Fourier transform technique for fringe analysis," Applied Optics, vol. 30, No. 28, pp. 4046-4055, 1991.

Kinoshita M. et al., "Optical Frequency-Domain Imaging Microprofilometry with a Frequency-Tunable Liquid-Crystal Fabry-Perot Etalon Device", *Applied Optics, Optical Society of America*, vol. 38, No. 34, Dec. 1, 1999, pp. 7063-7068.

L. Deck, "Absolute Distance Measurements Using FTPSI With a Widely Tunable IR Laser," Proc. SPIE, 4778, 218-226 (2002).

P. de Groot, 101-Frame Algorithm for Phase Shifting Interferometry, SPIE, vol. 3098, pp. 283-292 (1997).

\* cited by examiner

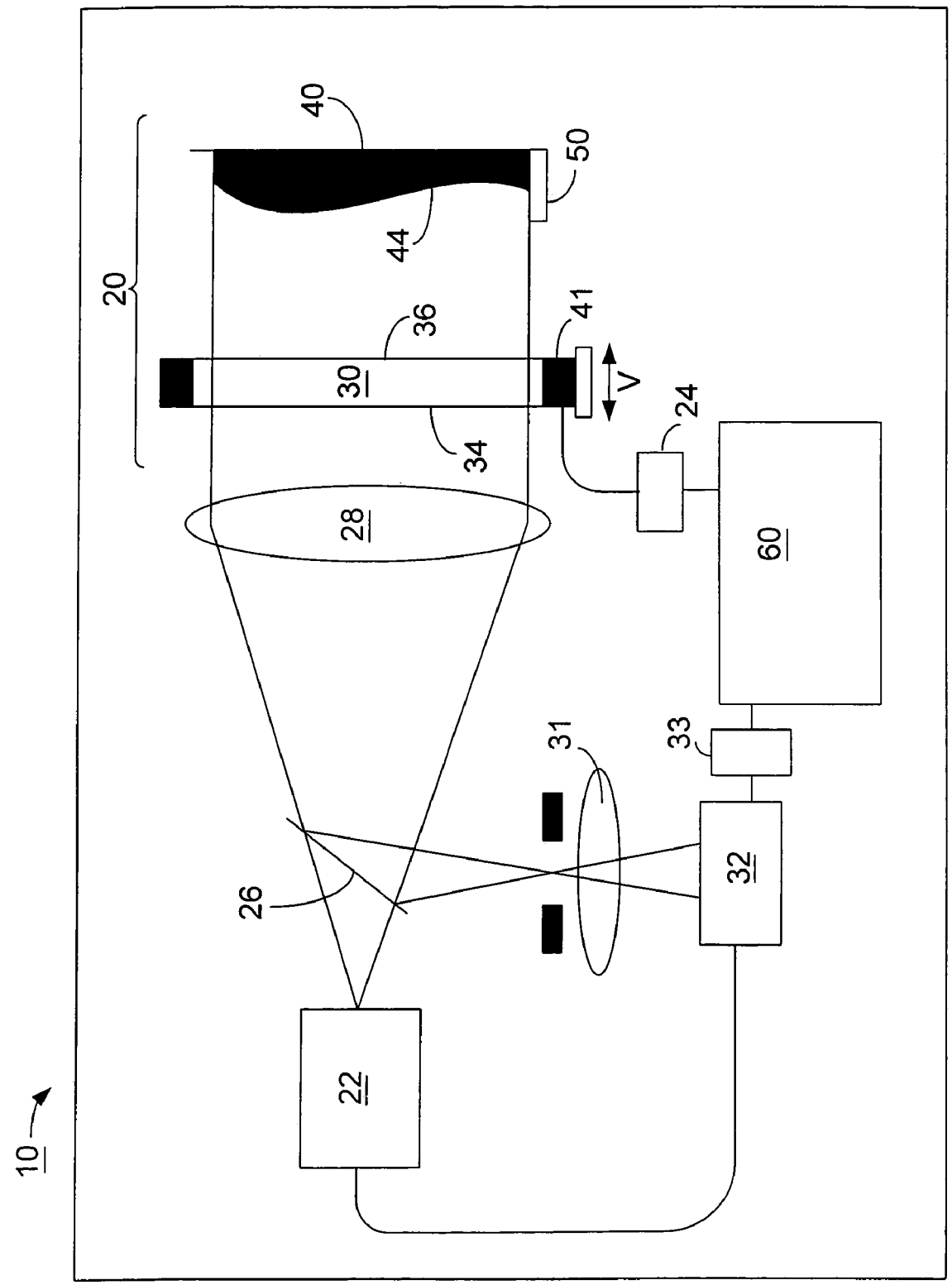

APPARATUS AND METHOD FOR MECHANICAL PHASE SHIFTING INTERFEROMETRY

CROSS-REFERENCE TO RELATED APPLICATIONS

This application claims priority to U.S. Provisional Application Ser. No. 60/339,098 entitled "Apparatus and Method for Mechanical Phase Shifting Interferometry" and filed on Dec. 10, 2001, the contents of which are incorporated herein by reference.

BACKGROUND

This invention relates to phase shifting interferometry and applications thereof.

Interferometric optical techniques are widely used to measure optical thickness, flatness, and other geometric and refractive index properties of precision optical components such as glass substrates used in lithographic photomasks.

For example, to measure the surface profile of a measurement surface, one can use an interferometer to combine a measurement wavefront reflected from the measurement surface with a reference wavefront reflected from a reference surface to form an optical interference pattern. Spatial variations in the intensity profile of the optical interference pattern correspond to phase differences between the combined measurement and reference wavefronts caused by variations in the profile of the measurement surface relative to the reference surface. Phase-shifting interferometry (PSI) can be used to accurately determine the phase differences and the corresponding profile of the measurement surface.

With PSI, the optical interference pattern is recorded for each of multiple phase-shifts between the reference and measurement wavefronts to produce a series of optical interference patterns that span a full cycle of optical interference (e.g., from constructive, to destructive, and back to constructive interference). The optical interference patterns define a series of intensity values for each spatial location of the pattern, wherein each series of intensity values has a sinusoidal dependence on the phase-shifts with a phase-offset equal to the phase difference between the combined measurement and reference wavefronts for that spatial location. Using numerical techniques known in the art, the phase-offset for each spatial location is extracted from the sinusoidal dependence of the intensity values to provide a profile of the measurement surface relative the reference surface. Such numerical techniques are generally referred to as phase-shifting algorithms.

The phase-shifts in PSI can be produced by changing the optical path length from the measurement surface to the interferometer relative to the optical path length from the reference surface to the interferometer. For example, the reference surface can be moved relative to the measurement surface. Alternatively, the phase-shifts can be introduced for a constant, non-zero optical path difference by changing the wavelength of the measurement and reference wavefronts. The latter application is known as wavelength tuning PSI and is described, e.g., in U.S. Pat. No. 4,594,003 to G. E. Sommargren.

SUMMARY

In general, in one aspect, the invention features an interferometry method including: i) forming an optical interference image by combining different portions of an optical wave front reflected from a pair of surfaces; ii) recording an interference signal at different locations of the optical interference image in response to varying the relative position of the two surfaces over a range of positions; iii) transforming the interference signal for at least one of the locations to produce a spectrum having a peak at a spectral coordinate corresponding to the variation in the relative position of the two surfaces over a range of positions; iv) identifying the spectral coordinate of the peak; and v) for each location, extracting the spectral phase of the interference signal at the coordinate of the peak. For example, the method may further include, for each of the different locations, determining a surface profile of one of the surfaces based on the spectral phase of the interference signal at each of the multiple locations.

Embodiments of the interferometry method can include any of the following features.

The interferometry method may further include determining a surface profile of one of the surfaces based on the spectral phase of the interference signal at each of the multiple locations.

The method may further include determining a wavelength of the optical wave front based on the identified spectral coordinate of the peak. The determined wavelength may be useful in determining the surface profile of one of the surfaces from the spectral phase of the interference signal.

Extracting the spectral phase of the interference signal for each location may include transforming the interference signal for each of the remaining locations to produce a corresponding spectrum having the peak. Alternatively, extracting the spectral phase of the interference signal for each location may include transforming the interference signal for each of the remaining locations with respect to the spectral coordinate of the peak.

The interference signal may be transformed using a frequency transform (e.g., a Fourier transform), in which case the spectral coordinate of the peak is a frequency. In such cases, it may be preferable that the interference signal is recorded as the relative position of the two surfaces are varied substantially linearly in time.

In other embodiments, the interference signal may be transformed with respect to the variations in relative position of the two surfaces, in which case the spectral coordinate of the peak is a wavevector.

The optical wave front may be derived from a source that produces multiple, narrow-band wavelengths, where each wavelength in the optical wave front produces a corresponding peak in the spectrum. In such cases, the method may further include identifying the spectral coordinate corresponding to each peak. The interferometry method may then further include determining a surface profile of one of the surfaces based on the spectral phase of the interference signal at each of the multiple locations for each of the peaks.

The optical wave front may be derived from a source and the range of positions over which the relative positions of the two surfaces are varied is smaller than the coherence length of the source.

The range of positions over which the relative positions of the two surfaces are varied may be smaller than five times a wavelength of the optical wave front.

The optical wave front may be derived from a source producing at least one narrow-band wavelength. For example, source may produce only one narrow-band wavelengths or it may produce multiple narrow-band wavelengths. The range of positions over which the relative positions of the two surfaces are varied may be smaller than the coherence length corresponding to any one of the narrow-band wavelengths produced by the source.

In general, in another aspect, the invention features an interferometry system including an interferometer which during operation directs different portions of an optical wave front derived from a light source to a pair of surfaces and recombines the different portions to form an optical interference image. The system also includes a phase-shifting component, coupled to at least one of the surfaces, a multi-element photo-detector positioned to record an interference signal at different locations of the optical interference image, and an electronic controller coupled to the phase shifting component and the photo-detector. During operation the controller: (i) causes the photo-detector record to the interference sign at the different locations as the phase shifting component varies the relative position of the two surfaces over a range of positions; (ii) transforms the interference signal for at least one of the locations to produce a spectrum having a peak at a spectral coordinate corresponding to the variation in the relative position of the two surfaces; (iii) identifies the spectral coordinate of the peak; and (iv) for each location, extracts the spectral phase of the interference signal at the coordinate of the peak.

Embodiments of the interferometry system can include any of the following features. The interferometer may be a Fizeau interferometer or a Michelson interferometer.

The phase-shifting component may be a transducer coupled to one of the surfaces.

During operation the controller, for each of the different locations, may further determine a surface profile of one of the surfaces based on the spectral phase of the interference signal at each of the multiple locations.

The controller may extract the spectral phase of the interference signal for each location by transforming the interference signal for each of the remaining locations to produce a corresponding spectrum having the peak and extracting the phase of the peak in each spectrum. Alternatively, the controller may extract the spectral phase of the interference signal for each location by transforming the interference signal for each of the remaining locations with respect to the spectral coordinate of the peak and extracting the phase of the spectrum and the phase of each of the transformed interference signals.

The controller may transform the interference signal using a frequency transform, e.g., a Fourier transform, in which case the spectral coordinate of the peak is a frequency. In such cases, it may be preferable that the controller causes the phase-shifting component to vary the relative position of the two surfaces substantially linearly in time.

In other embodiments, the controller may transform the interference signal with respect to the variations in the relative position of the two surfaces produced by the phase-shifting component, and wherein the spectral coordinate of the peak is a wavevector.

The system may also include the light source.

Moreover, the source may produce multiple, narrow-band wavelengths, where each wavelength in the optical wave front produces a corresponding peak in the spectrum. In such cases, the controller may further identify the spectral coordinate corresponding to each peak, and may then further determine a surface profile of one of the surfaces based on the spectral phase of the interference signal at each of the multiple locations for each of the peaks.

During operation, the controller may cause the phase-shifting component to vary the relative positions of the two surfaces over a range smaller than the coherence length of the source.

During operation, the controller may cause the phase-shifting component to vary the relative positions of the two surfaces over a range smaller than five times that of a wavelength of the optical wave front.

The source may produce at least one narrow-band wavelength. For example, the source may produce only one narrow-band wavelengths or it may produce multiple narrow-band wavelengths. During operation, the controller may cause the phase-shifting component to vary the relative positions of the two surfaces over a range smaller than the coherence length corresponding to any one of the narrow-band wavelengths produced by the source.

Embodiments of the invention may have any of the following advantages.

The method can determine the phase from any number of data frames in an acquisition, as the algorithm is not constrained to use a preset number of data points to determine the phase. Additionally, it can utilize data having any phase shift increment between frames, provided the cavity frequency can be resolved.

Systems employing the method may exhibit improved noise resistance, including resistance to vibration, non-linearity, intensity etc.

Unless otherwise defined, all technical and scientific terms used herein have the same meaning as commonly understood by one of ordinary skill in the art to which this invention belongs. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description.

DESCRIPTION OF DRAWINGS

FIG. 1 shows an embodiment of an interferometric system.

Like reference symbols in the various drawings indicate like elements.

DETAILED DESCRIPTION

The invention features a phase-shifting interferometry method and system. Some features of the invention are similar to the phase-shifting techniques described in commonly owned U.S. Provisional Application Ser. No. 60/339, 214 entitled "Frequency Transform Phase-Shifting Interferometry" and filed Dec. 10, 2001, the contents of which are incorporated herein by reference. The methods and systems disclosed in said provisional application are hereinafter referred to as FTPSI.

In some embodiments of FTPSI, optical frequency-tuned PSI data is analyzed in the frequency domain to produce spectrally separated frequency peaks each corresponding to a particular pair of surfaces in an interferometric cavity defined by multiple pairs of surfaces. Each frequency peak provides optical path length information about a corresponding pair of surfaces in the cavity. As a result, the interferometric data from such cavities provides simultaneous information about multiple surfaces. For example, information about any particular surface may be determined generically, and, unlike conventional PSI methods, do not require the interference to occur at specific frequencies. Additionally, this information may be determined without the need for adjacent data points to be sampled to produce a phase interval fixed by the cavity length of interest.

The present application extends the features of FTPSI, which was directed to, for example, frequency-tuned PSI data, to methods and systems in which a phase shifting component is used to vary the optical path length between a pair of surfaces. For example, such a component may be a transducer coupled to one of the surfaces to provide mechanical phase shifting. The following description provides some representative embodiments. Additional embodiments may include aspects and features corresponding to those described in the above-referenced provisional application on FTPSI.

A schematic diagram of a phase-shifting interferometric system 10 is shown in FIG. 1. Phase-shifting interferometric system 10 is adapted to measure the profile of a front surface 44 of a measurement object 40. Phase-shifting interferometric system 10 includes a Fizeau interferometer 20, a mount 50 for positioning measurement object 40 relative to interferometer 20, and a controller 60 such as a computer. Phase-shifting interferometric system 10 includes a light source 22 (e.g., a laser), a beam splitter 26, a collimating optic 28, an imaging optic 31, a CCD camera 32, and a frame grabber 33 for storing images detected by CCD camera 32. Also included in phase-shifting interferometric system 10 is a reference flat 30, which is mounted on a translatable stage 41. The translatable stage is in communication with controller 60 through a driver 24. The back surface of reference flat 30 defines a reflective reference surface 36 for the interferometer, whereas a front surface 34 of reference flat 30 has an antireflection coating and may be additionally or alternatively tilted with respect to back surface 36, so that reflections from front surface 34 do not take part in any subsequent measurements.

During operation, controller 60 causes driver 24 to move translatable stage 41, thereby dithering reference flat 30 back and forth and changing the optical path difference between front surface 44 and reflective reference surface 36 of reference flat 30. Controller 60 also causes frame grabber 33 to store an image of the optical interference detected by CCD camera 32 at multiple acquisition times during the phase shifting. Frame grabber 33 sends the images (i.e., interference signal) to controller 60 for analysis. In other embodiments, the measurement object is mounted on the translatable stage, and the front surface 44 is translated to phase shift the interference signal.

During operation, light source 22 directs light at a wavelength λ to beam splitter 26, which then directs the light to collimating lens 28 to collimate the light into a plane field. Reference surface 36 reflects a first portion of the light to form a reference wavefront, and surface 44 of measurement object 40 reflect an additional portion of the light to form a measurement wavefront. Lenses 28 and 31 then image the reference and measurment wavefronts onto CCD camera 32 where they form an optical interference image.

The CCD camera acquires the interference signal as a function of time as the positioned of the reference surface is varied linearly in time. The controller sorts the recorded intensity data according to the time at which the optical interference image was acquired. The controller Fourier transforms this data to the frequency domain, thereby generating a frequency spectrum for the data. The frequency spectrum exhibits a peak at $$f_c = \frac{2nv}{\lambda},$$

where n is the refractive index of the cavity (e.g., n=1 for air), λ is the wavelength of the light source, and v is the velocity at which the reference surface is translated. The phase φ(x,y) of the peak corresponds to the optical path length variation between the measurement and reference surfaces:

$$\varphi(x, y) = 4\pi n L(x, y)\frac{1}{\lambda} + \Phi, \tag{1}$$

where the surfaces are separated by a physical gap L and Φ is an overall constant phase. The x and y dependence of gap L and phase φ are shown explicitly in EQ. 1 to show the spatial variation in phase, which is captured by the different elements in the detector. In some embodiments, refractive index n may also have an x andy dependence. Extraction of this phase variation profile, or phase map, is the information that is typically of interest in phase shifting interferometry. For example, assuming that the surface profile of the reference surface is well-characterized, the surface profile of the measurement surface can be extracted from φ(x,y). Notably, by identifying the frequency of the peak, prior knowledge of the velocity v at which the reference surface is translated is not necessary. Alternatively, if the velocity is well known, prior knowledge of the wavelength is not necessary. Instead, we calculate the wavelength using $$\lambda = \frac{2nv}{f_c} \tag{2}$$

and insert the result into Eq.(1). This latter approach may be particularly useful when using a light source having uncertain wavelength, e.g., a filtered white light source, a light emitting diode, or a laser diode. Suitable high-precision mechanical translators that may provide accurate velocity data include PZT and other devices equipped with feedback via capacitive, optical or electronic displacement sensors.

In some embodiments, controller 60 transforms the interference signal from a subset of the detector elements (e.g., one or more elements) to generate the peak, identifies the frequency of the peak, Fourier transforms the interference signals from the remaining detector elements with respect to the peak frequency, and then extracts the phase of the transformed signals. Such a technique is computationally faster because a full spectrum is only calculated for a subset of the detector elements. Nonetheless, in other embodiments, the controller may calculate the full spectrum for each detector element and extract the phase corresponding to the peak in each spectrum.

Furthermore, in other embodiments, the interference signal for each detector element may be recorded with respect to the change in position of the reference surface itself. That change may be characterized in an absolute sense, e.g., the physical change in position, or with respect to some control variable, e.g., the voltage used to drive a piezoelectric transducer coupled to the reference surface. In such cases, the interference signal is Fourier transformed into a domain conjugate to the characterization of the reference surface position (e.g., a wavevector), rather than frequency. One advantage of such embodiments is that they obviate the need for linearity, or other calibrations, in the dithering rates. The analysis is otherwise similar.

It is noteworthy to contrast the technique with conventional phase extraction algorithms in PSI, which typically dictate a preset phase shift increment between acquisitions (e.g., $\pi/4$ or $\pi/2$) and extract a phase at a frequency corresponding to the preset phase-shift increment. In the present invention, however, no preset phase shift increment is necessary. Provided the phase shift increment is sufficiently small to resolve the modulation of the interference signal at $f_C$, any phase shift increment can be used between acquisitions. As a result, systems using the technique described herein reduce their sensitivity to calibration noise in the phase-shifting component. The techniques described herein can also be performed on an interference signal with any number of data points (e.g., frames) sufficient to resolve $f_C$, in contrast to some convention PSI algorithms. Acquiring a greater number of data points can reduce the systems sensitivity to noise including vibration, non-linearity, and intensity noise.

The light source for the phase-shifting interferometry system can be a laser such as a gas, solid-state, dye or semiconductor laser. The light source can also be a white-light source with a tunable narrow-band spectral filter. Accordingly, the light source typically provides a narrow-band wavelength suitable for phase-shifting interferometry.

Furthermore, in some embodiments the light source can operate at multiple nominal optical frequencies to resolve phase cycling ambiguities in the extracted phase profiles. For example, the light source can operate adjustably between the multiple lines of a HeNe, Argon, or diode laser. In some cases, the light sources can simultaneously provide multiple wavelengths of light (e.g., by combining the output of multiple diode lasers). The transform of the mechanically-phase shifted data should yield a $1^{st}$ order peak for each wavelength, from each of which a phase can be calculated. Fractional fringes or synthetic wavelengths can then be used to measure, e.g., surface heights with expanded range. These techniques are described in more detail in U.S. Pat. No. 5,398,113, which is incorporated by reference herein, in its entirety. Such measurements may be particularly useful when characterizing, for example, rough surfaces or performing step height measurements, etc.

Also, in some embodiments the light source can be coupled to the interferometer by an optical fiber.

In some embodiments, the light source for the PSI system can be a polarized light source (e.g., linearly polarized light). For example, the system can include a polarizing element in order to polarize the light from the lightsource. Each of the above-described measurement techniques can be performed as a function of the polarization state of the light. For example, the refractive index measurement technique could be performed for multiple different known polarization states (at least two polarization states, e.g., orthogonal polarization states). Variations in the refractive index, optical thickness, or relative optical thickness of a test object as a function of polarization can be related to the optical anisotropy of the object. Accordingly, in some embodiments the techniques described herein can be used to characterize the optical anisotropy (e.g., birefringence, dichroism, etc.) of a test object or cavity.

Furthermore, although the phase-shifting system in FIG. 1 included a Fizeau interferometer, other embodiments can employ an interferometer of a different type such as Twyman Green, Mach Zehnder, Michelson, Fabry-Perot, and grazing-incidence or unbalanced Mirau. Also, the interferometer can be a large aperture, microscope, or fiber optic sensor interferometer. Moreover, the measurement object can take on many forms. For example, the measurement object can be an optical flat, a photomask, a flat-panel display, or a silicon wafer (which could involve infrared illumination).

In any of the embodiments described above, the computer can include hardware, software, or a combination of both to control the other components of the system and to analyze the phase-shifted images to extract the desired information about the measurement object. The analysis described above can be implemented in computer programs using standard programming techniques. Such programs are designed to execute on programmable computers each comprising a processor, a data storage system (including memory and/or storage elements), at least one input device, at least one output device, such as a display or printer. The program code is applied to input data (e.g., phase-shifted images from a CCD camera) to perform the functions described herein and generate information (e.g., the topography of a selected surface), which is applied to one or more output devices. Each computer program can be implemented in a high-level procedural or object-oriented programming language, or an assembly or machine language. Each such computer program can be stored on a computer readable storage medium (e.g., CD ROM or magnetic diskette) that when read by a computer can cause the processor in the computer to perform the analysis described herein.

Furthermore, although the transform used in the above-described analysis is a Fourier transform, the invention is not so limited. Embodiments may also implement other types of transforms, such as Hilbert transforms.

A number of embodiments of the invention have been described. Nevertheless, it will be understood that various modifications may be made without departing from the spirit and scope of the invention.

What is claimed is:

1. An interferometry method comprising:
    forming an optical interference image by combining different portions of an optical wave front reflected from a pair of surfaces;
    recording an interference signal at different locations of the optical interference image in response to varying the relative position of the two surfaces over a range of positions;
    transforming the interference signal for at least one of the locations to produce a spectrum having a peak at a spectral coordinate corresponding to the variation in the relative position of the two surfaces, the spectral coordinate being different from a relative position value;
    identifying the spectral coordinate of the peak; and
    for each location, extracting the spectral phase of the interference signal at the coordinate of the peak.

2. The interferometry method of claim 1, further comprising determining a surface profile of one of the surfaces based on the spectral phase of the interference signal at each of the multiple locations.

3. The interferometry method of claim 1, wherein extracting the spectral phase of the interference signal for each location comprises transforming the interference signal for each of the remaining locations to produce a corresponding spectrum having the peak.

4. The interferometry method of claim 1, wherein extracting the spectral phase of the interference signal for each location comprises transforming the interference signal for each of the remaining locations with respect to the spectral coordinate of the peak.

5. The interferometry method of claim 1, wherein the interference signal is transformed using a frequency transform and the spectral coordinate of the peak is a frequency.

6. The interferometry method of claim 5, wherein the interference signal is recorded as the relative position of the two surfaces are varied substantially linearly in time.

7. The interferometry method of claim 6, wherein the frequency transform is a Fourier transform.

8. The interferometry method of claim 1, wherein the interference signal is transformed with respect to the variations in relative position of the two surfaces and the spectral coordinate of the peak is a wavevector.

9. An interferometry system comprising:
an interferometer which during operation directs different portions of an optical wave front derived from a light source to a pair of surfaces and recombines the different portions to form an optical interference image;
a phase-shifting component coupled to at least one of the surfaces;
a multi-element photo-detector positioned to record an interference signal at different locations of the optical interference image; and
an electronic controller coupled to the phase shifting component and the photodetector, wherein the controller is configured to: i) cause the photo-detector record to the interference sign at the different locations as the phase shifting component varies the relative position of the two surfaces over a range of positions; ii) transform the interference signal for at least one of the locations to produce a spectrum having a peak at a spectral coordinate corresponding to the variation in the relative position of the two surfaces, the spectral coordinate being different from a relative position value; iii) identify the spectral coordinate of the peak; and iv) for each location, extract the spectral phase of the interference signal at the coordinate of the peak.

10. The interferometry system of claim 9, wherein the interferometer is a Fizeau interferometer.

11. The interferometry system of claim 9, wherein the phase-shifting component is a transducer coupled to one of the surfaces.

12. The interferometry system of claim 9, wherein the controller is configured to, for each of the different locations, further determine a surface profile of one of the surfaces based on the spectral phase of the interference signal at each of the multiple locations.

13. The interferometry system of claim 9, wherein the controller is configured to extract the spectral phase of the interference signal for each location by transforming the interference signal for each of the remaining locations to produce a corresponding spectrum having the peak and extracting the phase of the peak in each spectrum.

14. The interferometry system of claim 9, wherein the controller is configured to extract the spectral phase of the interference signal for each location by transforming the interference signal for each of the remaining locations with respect to the spectral coordinate of the peak and extracting the phase of the spectrum and the phase of each of the transformed interference signals.

15. The interferometry system of claim 9, wherein the controller is configured to transform the interference signal using a frequency transform, and the spectral coordinate of the peak is a frequency.

16. The interferometry system of claim 15, wherein the controller is configured to cause the phase-shifting component to vary the relative position of the two surfaces substantially linearly in time.

17. The interferometry system of claim 16, wherein the frequency transform is a Fourier transform.

18. The interferometry system of claim 9, wherein the controller is configured to transform the interference signal with respect to the variations in the relative position of the two surfaces produced by the phase-shifting component, and wherein the spectral coordinate of the peak is a wavevector.

19. An interferometry method comprising:
forming an optical interference image by combining different portions of an optical wave front reflected from a pair of surfaces;
recording an interference signal at different locations of the optical interference image in response to varying the relative position of the two surfaces over a range of positions;
transforming the interference signal for at least one of the locations to produce a spectrum having a peak at a spectral coordinate corresponding to a frequency or wavevector indicative of the variation in the relative position of the two surfaces;
identifying the spectral coordinate of the peak; and
for each location, extracting the spectral phase of the interference signal at the coordinate of the peak.

20. An interferometry system comprising:
an interferometer which during operation directs different portions of an optical wave front derived from a light source to a pair of surfaces and recombines the different portions to form an optical interference image;
a phase-shifting component coupled to at least one of the surfaces;
a multi-element photo-detector positioned to record an interference signal at different locations of the optical interference image; and
an electronic controller coupled to the phase shifting component and the photo-detector, wherein the controller is configured to: i) cause the photo-detector record to the interference sign at the different locations as the phase shifting component varies the relative position of the two surfaces over a range of positions; ii) transform the interference signal for at least one of the locations to produce a spectrum having a peak at a spectral coordinate corresponding to a frequency or wavevector indicative of the variation in the relative position of the two surfaces; iii) identify the spectral coordinate of the peak; and iv) for each location, extract the spectral phase of the interference signal at the coordinate of the peak.

* * * * *